United States Patent [19]

Seng et al.

[11] 4,080,379
[45] Mar. 21, 1978

[54] SULPHONAMIDOSALICYLALDEHYDES

[75] Inventors: Florin Seng; Carl Wolfgang Schellhammer, both of Schildgen, Germany

[73] Assignee: Bayer Aktiengesellschaft, Leverkusen, Germany

[21] Appl. No.: 698,926

[22] Filed: Jun. 23, 1976

[30] Foreign Application Priority Data

Jun. 27, 1975 Germany .............................. 2528697

[51] Int. Cl.² .................. C07C 143/75; C07C 143/77; C07C 143/79
[52] U.S. Cl. ........................... 260/556 R; 260/556 A; 260/556 AR; 544/215
[58] Field of Search ....... 260/556 A, 556 R, 556 AR, 260/556 C, 248 NS

[56] References Cited

U.S. PATENT DOCUMENTS

| 1,876,955 | 9/1932 | Kalischer et al. | 260/556 AR |
| 3,271,412 | 9/1966 | Raue et al. | 260/308 |
| 3,317,603 | 5/1967 | Blance et al. | 260/248 NS |
| 3,660,487 | 5/1972 | Larsen et al. | 260/556 A |

FOREIGN PATENT DOCUMENTS 339,699  12/1930  United Kingdom ............ 260/556 A

OTHER PUBLICATIONS

Larsen et al., CA 71:30232k, (1969).

Primary Examiner—Daniel E. Wyman
Assistant Examiner—Thomas A. Waltz
Attorney, Agent, or Firm—Plumley and Tyner

[57] ABSTRACT

4-Sulphonamidosalicylaldehydes of the formula

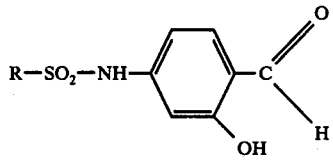

wherein

R represents an optionally substituted straight-chain or branched alkyl or cycloalkyl group or an optionally substituted aryl group, are valuable intermediates for the preparation of optical brighteners.

3 Claims, No Drawings

SULPHONAMIDOSALICYLALDEHYDES

The invention relates to new 4-sulphonamidosalicylaldehydes, a process for their preparation and their use as intermediates for the preparation of optical brighteners.

The new compounds correspond to the formula

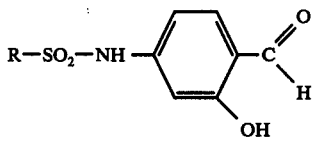
(I)

wherein
R can represent an optionally substituted straight-chain or branched alkyl or cycloalkyl group or an optionally substituted aryl group.

Examples of possible alkyl groups are saturated aliphatic radicals with 1 to 18 carbon atoms, preferably with 1 to 4 carbon atoms, which can be substituted by halogen atoms, nitro, or phenyl. Examples of such radicals are methyl, ethyl, propyl, isopropyl, butyl, isobutyl and tert.-butyl; the methyl radical is particularly preferred.

Possible cycloalkyl groups are those with 5 to 12 carbon atoms, preferably those with 5 or 6 carbon atoms, which can be substituted by halogen atoms, or alkyl with 1 to 4 C atoms, for example cyclopentyl, cyclohexyl, cycloheptyl, cyclooctyl, cyclononyl and cyclododecyl radicals, especially cyclopentyl and cyclohexyl radicals.

Preferred possible aryl groups are the phenyl or naphthyl radical, which, for example, can be substituted by halogen atoms, straight-chain or branched alkyl radicals which are optionally monosubstituted or polysubstituted by halogen, alkoxy groups with 1 to 4 carbon atoms, or optionally substituted aryl radicals, preferably phenyl radicals.

Examples of substituents on the phenyl and naphthyl radicals are fluorine, chlorine, bromine, iodine, methyl, ethyl, chloromethyl, trifluoromethyl, methoxy, ethoxy or phenyl.

Preferred aryl radicals are phenyl, chlorophenyl, tolyl, methoxyphenyl, trifluoromethylphenyl and fluorophenyl.

R can also represent a saturated aliphatic radical with 1 to 18 C atoms (straight chain or branched chain alkyl), which is optionally substituted by halogen, or phenyl; a cycloalkyl radical with 1 to 12 C atoms, which is optionally substituted by halogen, nitro, or alkyl with 1 to 4 C atoms; or a phenyl or naphthyl radical which is optionally substituted by halogen, $C_1-C_4$-alkyl which is optionally substituted by halogen, nitro, $C_1-C_4$-alkoxy or phenyl.

The compounds of the formula I are prepared according to the invention by subjecting 2,4-dioxo-hexahydro-6-[2-hydroxy-4-sulphonamideo-phenyl]-s-triazines of the formula II

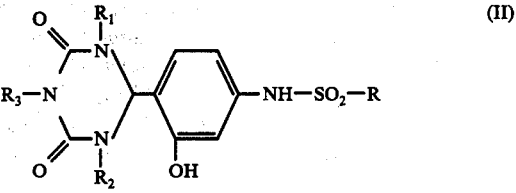
(II)

wherein
R has the abovementioned meaning and $R_1$, $R_2$ and $R_3$ represent $C_1-C_4$-alkyl, which is optionally substituted by phenyl, halogen, $C_1-C_4$-alkoxy or cyano, cyclohexyl or phenyl which is substituted by $C_1-C_4$-alkyl, trifluoromethyl, $C_1-C_4$-alkoxy, nitro or halogen, but in particular represent $C_1-C_4$-alkyl, preferably methyl, to alkaline saponification.

2,4-Dioxo-hexahydro-6-[2-hydroxy-4-sulphonamidophenyl]-s-triazines of the formula II are obtained from 2,4-dioxo-hexahydro-6-[2-hydroxy-4-aminophenyl]-s-triazines of the formula

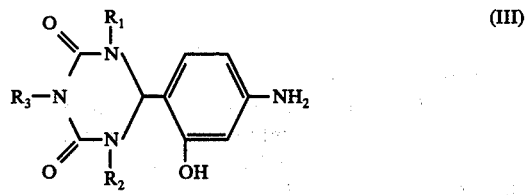
(III)

and sulphonic acid halides of the formula

(IV)

wherein
X represents fluorine, chlorine or bromine and R, $R_1$, $R_2$ and $R_3$ have the abovementioned meaning.

2,4-Dioxo-hexahydro-6-[2-hydroxy-4-sulphonamidophenyl]-s-triazines of the formula II are prepared according to processes which are known from the literature, such as are described in Houben-Weyl, Methoden der organischen Chemie (Methods of Organic Chemistry), IX, page 605.

The saponification of the 2,4-dioxo-hexahydro-6-[2-hydroxy-4-sulphonamidphenyl]-s-triazines of the formula II is carried out in aqueous alkali using 4 to 10 mols, preferably 6 to 8 mols, of alkali per mol of hexahydro-s-triazine at temperatures of 90° to 120° C, preferably 95° to 112° C.

2,4-Dioxo-hexahydro-6-[2-hydroxy-4-aminophenyl]-s-triazines of the formula III are prepared starting from corresponding substituted biurets, which are reacted with formaldehyde, or agents which release formaldehyde, to give 2,4-dioxo-hexahydro-1,3,5-triazines. Halogenation of these compounds, for example with elementary halogen, such as chlorine and bromine, or also with sulphuryl chloride, sodium hypochloride or N-bromosuccinimide, gives 2,4-dioxo-1,2,3,4-tetrahydro-1,3,5-triazinium halides, which are reacted with m-aminophenol, the reaction appropriately being carried out in a polar solvent at temperatures between 0° and 100° C in the presence of a stoichiometric amount of a base, such as sodium carbonate or triethylamine, in order to neutralise the hydrogen halide acid which is liberated.

Examples of 2,4-dioxo-1,2,3,4-tetrahydro-1,3,5-triazinium salts which may be mentioned are: 1,3,5- trimethyl-, 1,5-diethyl-3-methyl-, 1,5-dicyclohexyl-3-methyl-, 1,5-dimethyl-3-isopropyl-, 1,5-diisopropyl-3-methyl-, 1,5-dibenzyl-3-methyl-, 1,5-dimethyl-3-phenyl-, 1,5-di-(3-trifluoromethyl-phenyl)-3-methyl-, 1-phenyl-3,5-dimethyl-, 1-(3-trifluoromethyl-phenyl)-3,5-dimethyl-, 1-(trifluoromethyl-4-chlorophenyl)-3,5-dimethyl-, 1,5-di-(cyanomethyl)-3-methyl-, 1,5-di-tert.-butyl-3-methyl-, 1,5-di-n-butyl-3-methyl-, 1,5-di-isobutyl-3-methyl- and 1,5-di-n-propyl-3-methyl-2,4-dioxo-1,2,3,4-tetrahydro-3-triazinium chloride or bromide.

The sulphoamidosalicylaldehydes according to the invention are valuable intermediates for the preparation of optical brighteners of the coumarin series according to processes which are in themselves known, such as are known, for example, from German Patent Specification No. 1,296,121.

The reaction time is 2 to 10, preferably 4 to 8, hours.

Alkalis which can be used are the oxides and hydroxides of the alkali metals and alkaline earth metals. Examples which may be mentioned are sodium hydroxide, potassium hydroxide, calcium oxide and barium hydroxide.

After the reaction, the 4-sulphonamidosalicylaldehydes are obtained in a crystalline form by acidifying the reaction solution.

Acids which can be used here are mineral acids, such as hydrochloric acid, sulphuric acid or phosphoric acid, but also organic acids, such as acetic acid or aromatic or aliphatic sulphonic acids.

EXAMPLE 1

2,4-Dioxo-hexahydro-1,3,5-trimethyl-6-[2-hydroxy-4-benzenesulphonamido-phenyl]-s-triazine.

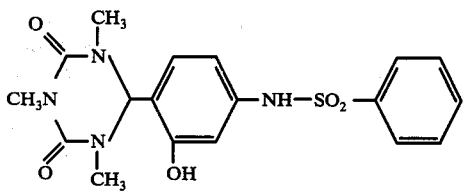

264 g (1 mol) of 2,4-dioxo-1,3,5-trimethyl-6-[2-hydroxy-4-aminophenyl]-s-triazine, together with 84 g (1 mol) of sodium bicarbonate are initially introduced into 1.8 l of water. 212 g (1.2 mols) of benzenesulphochloride are added dropwise in the course of 30 minutes and the mixture is stirred for a further 3.5 hours. It is then filtered and 374 g (93%) of 2,4-dioxo-hexahydro-1,3,5-trimethyl-6-[2-hydroxy-4-benzenesulphonamido-phenyl]-s-triazine are obtained as white crystals which, after trituration with methanol, melt at 220° to 222° C. When the filtrate is neutralised, 17 g. (0.064 mol) of the starting material are recovered.

The following were prepared analogously:

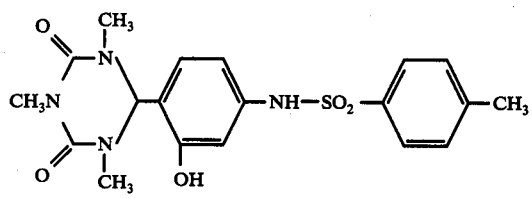

Melting point: 240 to 245° C

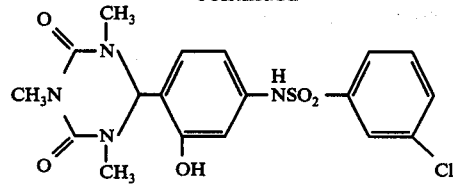

Melting point: 264° C

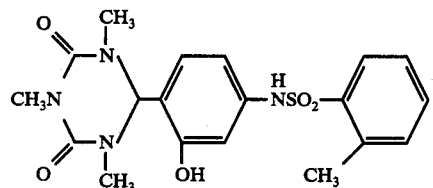

Melting point: 263° C

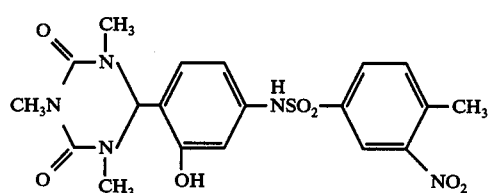

Melting point: 270° C

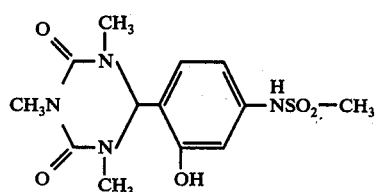

Melting point: 253° C

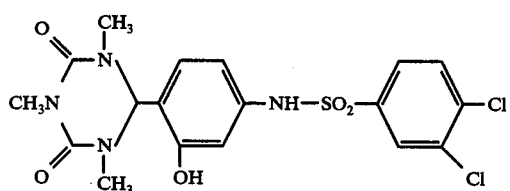

Melting point: >260° C

EXAMPLE 2

2,4-Dioxo-hexahydro-1,3,5-trimethyl-s-triazine 145 g (1 mol) of 1,3,5-trimethyl-biuret and 30 g of paraformaldehyde are heated together with 5 ml of concentrated hydrochloric acid to 70° C for 5 hours. The liquid contents of the flask are then poured onto a dry metal sheet and, after solidification, recrystallised from cyclohexane. This gives 154 g (98%) of 2,4-dioxo-hexahydro-1,3,5-trimethyl-s-triazine of melting point 88° C to 90° C.

EXAMPLE 3

2,4-Dioxo-1,2,3,4-tetrahydro-1,3,5-trimethyl-s-triazinium bromide 15.7g (0.1 mol) of 2,4-dioxo-hexahydro-1,3,5-trimethyl-s-triazine are dissolved in 30 ml of methylene chloride and 24 g (0.15 mol) of bromine are added dropwise. During this addition, the temperature is kept at between 20° C and 30° C by cooling. After a few minutes the addition product of bromine with 2,4-dioxo-1,2,3,4-tetrahydro-1,3,5-trimethyl-s-triazinium bromide separates out in the form of orange colored crystals. These are filtered off and recrystallised from isopropanol. This gives 20 g (85%) of 2,4-dioxo-1,2,3,4-tetrahydro-1,3,5-trimethyl-s-triazinium bromide as white crystals which melt at 217° C.

EXAMPLE 4

2,4-Dioxo-hexahydro-1,3,5-trimethyl-6-[2-hydroxy-4-amino-phenyl]-s-triazine

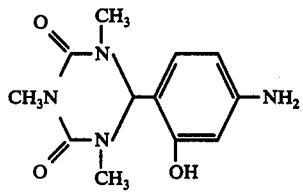

23.6 g (0.1 mol) of 2,4-dioxo-1,2,3,4-tetrahydro-1,3,5-trimethyl-s-triazinium bromide are dissolved in 50 ml of water and 10.9 g (0.1 mol) of m-aminophenol are added. After a few minutes, a clear solution has formed. 8 g of sodium bicarbonate are added to the solution. 25 g (89%) of 2,4-dioxo-hexahydro-1,3,5-trimethyl-6-[2-hydroxy-4-amino-phenyl]-s-triazine precipitate out as white crystals, which, after they have been dissolved in aqueous hydrochloric acid and the solution has been clarified with active charcoal and neutralised, melt at 240° C.

EXAMPLE 5

4-Benzenesulphonamidosalicylaldehyde 432 g (1 mol) of 2,4-dioxo-hexahydro-1,3,5-trimethyl-6-[2-hydroxy-4-benzenesulphonamido-phenyl]-s-triazine (93.5% pure product) are introduced into a solution of 280 g (7 mols) of sodium hydroxide in 600 ml of water. The mixture is boiled under reflux for 6 hours, under nitrogen. A pale brown solution is formed, from which individual small crystals separate out. The contents of the flask are then poured onto a mixture of 700 ml of concentrated hydrochloric acid and 2 kg of ice and the yellow product which has separated out is filtered off. After washing with water and drying at 80° C, 274 g of 4-benzenesulphonamidosalicylaldehyde with a melting point of 150° to 157° C are obtained. According to the oxime titration, the aldehyde is 94.8% pure and the yield is thus 93.6%. After redissolving in xylene (1 : 10), the aldehyde is obtained as colorless crystals with a melting point of 160° to 163° C.

The following were prepared analogously:

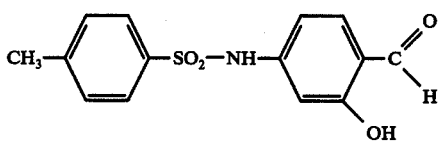

Melting point 185 to 188° C

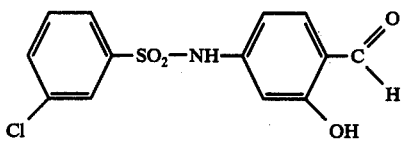

-continued
Melting point 176 to 180° C

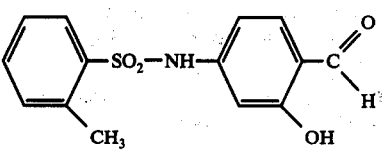

Melting point 199 to 202° C

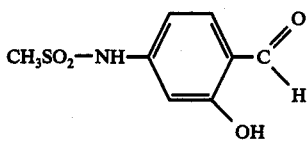

Melting point 143 to 145° C

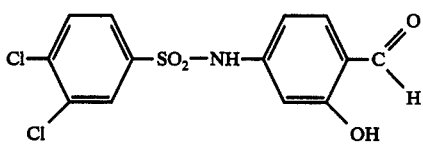

Melting point 112 to 113° C

We claim:
1. Salicylaldehyde of the formula

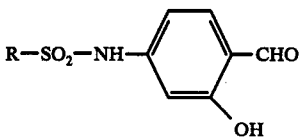

wherein
R is alkyl of 1 to 18 carbon atoms; alkyl of 1 to 18 carbon atoms substituted by halogen, or phenyl; cycloalkyl of 1 to 12 carbon atoms; cycloalkyl of 1 to 12 carbon atoms substituted by halogen, nitro, or alkyl of 1 to 4 carbon atoms; phenyl; naphthyl; or phenyl or napthyl substituted by halogen, by alkyl of 1 to 4 carbon atoms; or by alkyl of 1 to 4 carbon atoms substituted by halogen, nitro, alkoxy of 1 to 4 carbon atoms, or phenyl.

2. Process for the preparation of a salicylaldehyde of the formula

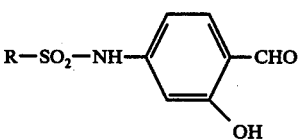

comprising the alkaline saponification of a 2,4-dioxo-hexahydro-6-[2-hydroxy-4-sulphonamidophenyl]-s-triazine of the formula

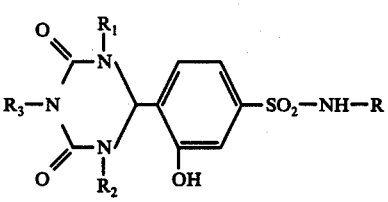

wherein
R is alkyl of 1 to 18 carbon atoms; alkyl of 1 to 18 carbon atoms substituted by halogen, or phenyl; cycloalkyl of 1 to 12 carbon atoms; cycloalkyl of 1 to 12 carbon atoms substituted by halogen, nitro, or alkyl of 1 to 4 carbon atoms; phenyl; naphthyl; or phenyl or naphthyl substituted by halogen, by alkyl of 1 to 4 carbon atoms, or by alkyl of 1 to 4 carbon atoms substituted by halogen, nitro, alkoxy of 1 to 4 carbon atoms, or phenyl.

3. The process of claim 2 in which said alkaline saponification is carried out at 90° to 120° C in aqueous alkali using 4 to 10 moles of alkali per mole of said 2,4-dioxo-hexahydro-6-[2-hydroxy-4-sulphamidophenyl]-s-triazine.

* * * * *